United States Patent [19]

Toyota et al.

[11] Patent Number: 5,216,172
[45] Date of Patent: Jun. 1, 1993

[54] 1,4-DIHYDROPYRIDINE-4-ARYL-2,6-DIMETHYL-3,5-DICARBOXYLATES USEFUL AS AGENTS AGAINST DRUG RESISTANT TUMOR CELLS

[75] Inventors: Kouzou Toyota, Kawasaki; Hisashi Shinkai, Tokyo; Hirozumi Eto, Kawasaki; Akira Kamimura, Kawasaki; Chikahiko Eguchi, Kawasaki; Koji Ohsumi, Kawasaki; Takashi Tsuruo, Tokyo, all of Japan

[73] Assignees: Ajinomoto Co., Inc.; Japanese Foundation for Cancer Research, both of Tokyo, Japan

[21] Appl. No.: 647,192

[22] Filed: Jan. 28, 1991

Related U.S. Application Data

[63] Continuation of Ser. No. 314,864, Feb. 24, 1989, abandoned.

[30] Foreign Application Priority Data

Feb. 24, 1988 [JP] Japan ................... 63-41369

[51] Int. Cl.⁵ ................ C07D 213/55; C07D 213/57; A61K 31/44
[52] U.S. Cl. ................... 546/321; 546/286
[58] Field of Search ........................ 546/321

[56] References Cited

U.S. PATENT DOCUMENTS

| | | | |
|---|---|---|---|
| 3,511,847 | 5/1970 | Loev et al. | 546/321 |
| 4,284,634 | 8/1981 | Satu | 514/344 |
| 4,520,131 | 5/1985 | Loev et al. | 514/156 |

FOREIGN PATENT DOCUMENTS

| | | | |
|---|---|---|---|
| 0009206 | 4/1980 | European Pat. Off. | 544/33 |
| 0111453 | 6/1984 | European Pat. Off. | 544/60 |
| 0123850 | 11/1984 | European Pat. Off. | 514/356 |
| 0234776 | 9/1987 | European Pat. Off. | 546/321 |
| 0245919 | 11/1987 | European Pat. Off. | 546/321 |
| 1813436 | 10/1970 | Fed. Rep. of Germany | 546/321 |

(List continued on next page.)

OTHER PUBLICATIONS

Chemical & Pharmaceutical Bulletin, vol. 27, No. 6, Jun. 1979, pp. 1426–1440; M. Iwanami et al., "Synthesis of new water-soluble dihydropyridine vasodilators".

(List continued on next page.)

*Primary Examiner*—Alan L. Rotman
*Attorney, Agent, or Firm*—Sughrue, Mion, Zinn, Macpeak & Seas

[57] ABSTRACT

Agents against drug-resistant tumor cells comprising a 1,4-dihydropyridine derivative represented by the following formula (I):

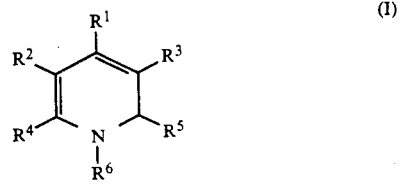

wherein $R^1$ is an aryl group which may be substituted;

$R^2$ and $R^3$, which may be the same or different, each is a member selected from the group consisting of an alkyl group, an alkyloxycarbonyl group, an aryloxycarbonyl group, an aralkyloxycarbonyl group, an aminocarbonyl group, a hydroxycarbonyl group, a formyl group, and a cyano group, each of which may be substituted;

$R^4$ and $R^5$ is a hydrogen atom or a member selected from the group consisting of a lower alkyl group, a hydroxymethyl group, a cyano group, an amino group, a formyl group, and a halogen atom; and $R^6$ is a member selected from the group consisting of an alkyl group, an aralkyl group, an alkoxycarbonyl group and an aralkyloxycarbonyl group, each of which may be substituted and the alkyl moiety in each may also contain a double bond, a triple bond or a hetero atom and combinations thereof with anticancer agents.

3 Claims, No Drawings

FOREIGN PATENT DOCUMENTS

| | | |
|---|---|---|
| 1963186 | 6/1971 | Fed. Rep. of Germany ...... 546/250 |
| 1963188 | 6/1971 | Fed. Rep. of Germany ...... 546/321 |
| 2005116 | 9/1971 | Fed. Rep. of Germany ...... 546/263 |
| 2013431 | 10/1971 | Fed. Rep. of Germany ...... 546/250 |
| 2210672 | 9/1973 | Fed. Rep. of Germany ...... 546/321 |
| 2218644 | 10/1973 | Fed. Rep. of Germany ...... 544/360 |
| 2228363 | 1/1974 | Fed. Rep. of Germany ...... 546/250 |
| 2228377 | 1/1974 | Fed. Rep. of Germany ...... 544/333 |
| 2428415 | 1/1975 | Fed. Rep. of Germany ...... 544/124 |
| 2444654 | 3/1975 | Fed. Rep. of Germany ...... 546/321 |
| 2908738 | 9/1979 | Fed. Rep. of Germany ...... 546/321 |
| 2302093 | 9/1976 | France ............................ 546/321 |
| 1430961 | 4/1976 | United Kingdom ................ 546/284 |
| 1438931 | 6/1976 | United Kingdom ................ 546/321 |

OTHER PUBLICATIONS

Chemical Abstracts, vol. 90, No. 15, Apr. 9, 1979, p. 623, left-hand column, Abstract No. 121362m, Columbus, Ohio, US; A. Sausins et al., "N-Alkylation of 1,4-dihydropyridine-3,5-dicarboxylic acid esters", Khim., Geterotsikl. Soedin. 1978, No. 11, pp. 1508-1513.

Patent Abstracts of Japan, vol. 7, No., 273 (C-198)(1418), Dec. 6, 1983.

Patent Abstracts of Japan, vol. 9, No. 188 (C-295)(1911), Aug. 3, 1985.

1,4-DIHYDROPYRIDINE-4-ARYL-2,6-DIMETHYL-3,5-DICARBOXYLATES USEFUL AS AGENTS AGAINST DRUG RESISTANT TUMOR CELLS

This is a continuation of application Ser. No. 07/314,864 filed Feb. 24, 1989, now abandoned.

FIELD OF THE INVENTION

This invention relates to compositions and agents against tumor cells with acquired multidrug resistance, which are effective in inhibiting the loss of administered antitumor agents from tumor cells, to 1,4-dihydropyridine derivatives which are compounds having such an effect, and to a method of enhancing the anti-cancer effect of anti-cancer agents.

BACKGROUND OF THE INVENTION

Conventional chemotherapy for the treatment of cancers involves the critical problem of "acquired drug resistance" (i.e., the anti-cancer agent being administered becomes ineffective during treatment) and, particularly, the problem of "multidrug resistance" (i.e., acquired resistance to several kinds of anti-cancer agents). Specifically, solid cancer is generally resistant to anticancer agents. Disappearance of the activity of anticancer agents during therapy is widely experienced, and the mechanism underlying this phenomenon has been experimentally proven to be due to the acquisition of resistance of the cancer cells to anticancer agents. Currently, the acquisition of resistance is considered to be the greatest cause of failure of chemotherapy.

Among the aspects of acquired resistance, a phenomenon of biochemical interest is multiple drug resistance. This phenomenon has been seen in many cancer cells. For example, the table set forth below shows the degree of resistance of an adriamycin resistance cell line of human myeloma leukemia K562 to various anticancer agents.

| Degree of resistance of adriamycin-resistant human myeloma leukemia cell line to various anticancer agents | |
|---|---|
| Drug | Degree of resistance (fold) |
| Adriamycin | 134 |
| THP-adriamycin[a] | 42 |
| Guanomycin | 80 |
| Aclacinomycin A | 7.3 |
| Mitomycin C | 12 |
| Actinomycin D | 108 |
| Mitozantron | 80 |
| Algomycin | 26 |
| AG-2 | 185 |
| Menogarol | 76 |
| Vincristine | 628 |
| Vinblastine | 122 |
| Vindesin | 841 |
| Etoposide | 44 |
| Meitancin | 74 |
| Taxol | >3,800 |

[a]4-o-tetrahydropyranyl-adriamycin

Among the cytological changes related to the acquisition of resistance, the changes which can be easily analyzed biochemically are those induced by mutations. Many chemotherapeutic agents produce chromosomal aberrations (mutations) and induce resistance, as shown in the table below.

| Chromosomal changes related to resistance induced by anticancer agents | | |
|---|---|---|
| Drug | Cancer Cell | Chromosomal Change |
| 6-Mercaptopurine | Human lymphocytes | Structure and number |
| 5-Fluorouracil | Human colon | Structure |
| Cytosine arabinoside | Leukemia | Structure |
| Methotrexate | Human bone marrow Mouse fetus | Structure and number |
| Melphalan | Human lymphocytes | Structure |
| Cyclophosphamide | Human lymphocytes Mouse cells | Structure and number |
| Cisplatin | Human lymphocytes | Structure |
| Actinomycin D | Human lymphocytes | Structure |
| Daunomycin | Human lymphocytes | Structure and number |
| Adriamycin | Human lymphocytes Mouse cells | Structure and number |
| Bleomycin | Human lymphocytes Mouse cells | Structure |
| Mitomycin C | Human lymphocytes Mouse cells | |
| Vincristine | Human lymphocytes | Number |
| Vinblastine | Human lymphocytes Hamster cells | Structure and number |

Cancer cells that show multiple drug resistance have interesting characteristics, including 1) exhibiting resistance to other anticancer agents (cross-resistance), 2) promoting the excretion of the anticancer agent and consequently, lowering the concentration of the anticancer agent in the cells, and 3) exhibiting changes in the membrane proteins.

For example, vinkaloid, colchicine and meitancin anticancer agents show cross-resistance to anthracyclin, and actinomycin agents which intercalate with DNA, and these drugs also show cross-resistance to the inhibitors of protein synthesis, puromycin and emetine. In the cells that show cross-resistance, the intracellular concentrations of colchicine, vincristine and vinblastine are kept low, often by the promotion of excretion, and partly by a change in the binding to the target, as shown in the table below.

| Pharmacological action in the cells showing cross resistance to vincaalkaloid drugs | | |
|---|---|---|
| Resistant Cell | Drug | Pharmacological action of drug |
| Colchicine-resistant Chinese hamster | Colchicine | Decrease penetrability |
| Colchicine-resistant cell | Colchicine | Decrease in incorporation and retention, changes in binding |
| Meitancin-resistant 3T3 | Colchicine | Decreased incorporation, lowered binding to surface |
| Vincristine-resistant P388 | Vincristine | Decrease in incorporation, decreased retention |
| Vincristine-resistant Ehrlich | Vincristine | Decreased incorporation due to accelerated excretion and decrease in retention |
| Vincristine-resistant P388 | Vincristine | Decreased incorporation, accelerated excretion |
| Vinblastine-resistant Ehrlich | Vinblastine | Decreased incorporation |
| Vinblastine-resistant CEM | Vinblastine | Decreased incorporation and retention, changes in binding |

As shown in the table above, the most peculiar characteristic of multiple drug resistance is the acceleration of membrane transport, especially the promotion of excretion.

Administration of larger quantities of an anti-cancer agent to prevent the decrease in the amount of agent in the tumor cells is not an effective remedy because side-effects are more severe.

To overcome this problem, calcium antagonists have been found to inhibit the accelerated extracellular excretion of anticancer agents by resistance cells. As a result, a large amount of the anticancer agents are accumulated in the resistance cells, resulting in the death of the cells. However, this method has the disadvantage that the effective amount of calcium antagonist exhibits an excessive hypotensive action and shows high toxicity.

Hence, there has been a demand for the development of new agents with higher therapeutic effect and lower toxicity.

SUMMARY OF THE INVENTION

After extensive research on a great variety of 1,4-dihydropyridine derivatives for compounds that meet the above-mentioned requirements, it has now been found that compounds represented by the following general formula (I)

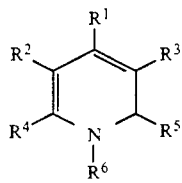

(I)

where
$R^1$ is an aryl group (e.g., aryls of 6 to 14 carbon atoms such as phenyl and naphthyl) which may optionally have a substituent group (or groups) (e.g., having up to 5 carbon atoms therein);
$R^2$ and $R^3$, which may be the same or different, each is an organic group selected from alkyl groups (e.g., lower alkyls of 1 to 5 carbon atoms such as methyl, ethyl, iso-propyl and tert-butyl), alkyloxycarbonyl groups (the alkyl moiety being, for example, a lower alkyl of 1 to 5 carbon atoms with examples being as described above), aryloxycarbonyl groups (e.g., aryloxy carbonyls with 6 to 14 carbon atoms in the aryloxy moiety thereof such as phenyloxycarbonyl and naphthyloxycarbonyl), aralkyloxycarbonyl groups (e.g., those having 1 to 5 carbon atoms in the alkyl moiety thereof and 6 to 14 carbon atoms in the aryl moiety thereof such as benzyloxycarbonyl), aminocarbonyl groups (e.g., aminocarbonyls which may be substituted, for example, with substituent groups of up to 14 carbon atoms such as methyl, dimethyl and dibenzyl), a hydroxycarbonyl group, a formyl group and a cyano group, which groups may optionally have a substituent group or groups;
$R^4$ and $R^5$, which may be the same or different, each is a hydrogen atom or a member selected from lower alkyl groups (e.g., having 1 to 5 carbon atoms such as methyl and ethyl), hydroxymethyl, cyano, amino (e.g., aminocarbonyls which may be substituted, for example, with substituent groups of up to 14 carbon atoms such as methyl, dimethyl and dibenzyl) and formyl groups, and halogen atoms (e.g., fluorine, chlorine, bromine and iodine); and
$R^6$ is an alkyl group (e.g., an alkyl of 1 to 10 carbon atoms such as methyl, ethyl, iso-propyl, tert-butyl, octyl and decyl), an aralkyl group (e.g., having 1 to 10 carbon atoms in the alkyl moiety thereof and 6 to 14 carbon atoms in the aryl moiety thereof such as phenylalkyl), an alkoxycarbonyl group (the alkyl moiety being, for example, a lower alkyl of 1 to 5 carbon atoms as described above), or an aralkyloxycarbonyl group (e.g., having 1 to 5 carbon atoms in the alkyl moiety thereof and 6 to 14 carbon atoms in the aryl moiety thereof such as phenylalkyloxycarbonyl), where each of these groups may optionally have a substituent group or groups, and the alkyl moiety in each may optionally contain a double bond(s), a triple bond(s) or a hetero atom(s) such as oxygen, nitrogen or sulfur show a powerful action against drug-resistant tumor cells in enhancing the effect of the anti-cancer agents against such cells.

DETAILED DESCRIPTION OF THE INVENTION

The aryl group for $R^1$ can be an aryl group having 6 to 14 carbon atoms, such as phenyl or naphthyl. Examples of the substituent(s) on the aryl group represented by $R^1$ (e.g., phenyl and naphthyl) include halogen atoms (e.g., fluorine, chlorine, bromine and iodine), lower alkyl groups (e.g., having 1 to 5 carbon atoms such as methyl, ethyl, propyl, isopropyl and tert-butyl), a hydroxy group, lower alkoxy groups (e.g., having 1 to 5 carbon atoms in the alkyl moiety thereof such as methoxy, ethoxy, iso-propoxy and tert-butoxy), a benzyloxy group, alkylene dioxy groups of 1 to 3 carbon atoms, and nitro, amino (e.g., which may be substituted, for example, with substituent groups of up to 14 carbon atoms such as methyl, dimethyl and dibenzyl), cyano and trifluoromethyl groups.

$R^2$ and $R^3$ each represent a methyl, hydroxymethyl, methoxycarbonyl, ethoxycarbonyl, methoxyethyloxycarbonyl, isopropoxycarbonyl, tert-butoxycarbonyl, phenoxycarbonyl, benzyloxycarbonyl, aminocarbonyl, methylaminocarbonyl, benzylaminocarbonyl, hydroxycarbonyl, formyl, or cyano group. When $R^6$ is an aralkyl group, it may optionally be a substituted or unsubstituted phenyl or phenoxy group at the end of the alkylene moiety, and this alkylene moiety may optionally contain a substituent group (or groups) selected from lower alkyls of 1 to 5 carbon atoms (e.g., methyl, ethyl and iso-propyl), a cyano group and an oxo group, and may also contain a carbon-carbon double bond(s) or triple bond(s) (representing an alkenylene group of 3 to 9 carbon atoms or an alkynylene group of 3 to 9 carbon atoms). The substituent selected from halogen atoms (e.g., fluorine, chlorine, bromine and iodine), lower alkyls of 1 to 5 carbon atoms (e.g., methyl, ethyl, propyl and isopropyl), a hydroxy group, alkyloxy groups of 1 to 5 carbon atoms (e.g., methoxy and ethoxy), alkylene dioxy groups of 1 to 3 carbon atoms, a benzyloxy group and, nitro, amino which may be substituted with a group(s) with up to 14 to carbon atoms such as methyl, dimethyl and dibenzyl, cyano and trifluoromethyl groups.

Of the 1,4-dihydropyridine derivatives of formula (I), those which are represented by the following general formula (II) are novel compounds with high activity providing new physiological activities:

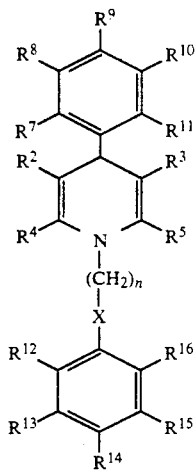

(II)

wherein $R^2$ and $R^3$ are as defined above;

$R^7$, $R^8$, $R^9$, $R^{10}$ and $R^{11}$, which may be the same or different, each represents a hydrogen atom or a member selected from halogen atoms (e.g., fluorine, chlorine, bromine and iodine), lower alkyl groups of 1 to 5 carbon atoms (e.g., methyl, ethyl, propyl and iso-propyl), a hydroxy group, lower alkyloxy groups (e.g., having 1 to 5 carbons in the alkyl moiety thereof, such as, methoxy and ethoxy), and nitro, amino (which may be substituted with a group having up to 14 carbon atoms such as methyl, dimethyl and dibenzyl), cyano and trifluoromethyl groups;

n represents an integer of 2 to 9;

X is a methylene group, an oxygen atom, a nitrogen atom or a carbonyl group, wherein the methylene group may optionally have a substituent group selected from lower alkyls of 1 to 5 carbon atoms (e.g., methyl, ethyl, propyl and iso-propyl), a cyano group and an oxo group; and $R^{12}$, $R^{13}$, $R^{14}$, $R^{15}$ and $R^{16}$, which may be the same or different, each represents a hydrogen atom or a member selected from halogen atoms (e.g., fluorine, chlorine, bromine and iodine), lower alkyl groups of 1 to 5 carbon atoms (methyl, ethyl, propyl and iso-propyl), a hydroxy group, lower alkyloxy groups of 1 to 5 carbon atoms (e.g., methoxy and ethoxy), alkylene dioxy groups of 1 to 3 carbon atoms, a benzyloxy group, and nitro, amino (which may be substituted with a group having up to 14 carbon atoms such as methyl, dimethyl and dibenzyl), cyano and trifluoromethyl groups.

The compounds of this invention may also be in the form of salts thereof. Suitable examples of such salts include pharmaceutically acceptable salts. For example, if the compound is acidic, suitable salts include salts of alkali metals such as sodium and potassium, alkaline earth metals such as calcium, inorganic bases such as ammonia, organic bases such as cyclohexylamine, N-methyl-D-glucosamine, basic amino acids, for example, lysine, arginine. Several kinds of cations may be employed if desired.

When the compound is basic, suitable salts include salts of acidic materials such as mineral acids, for example, hydrochloric acid and sulfuric acid, organic acids, for example, tartaric acid and malic acid, acidic amino acids, for example, glutamic acid and aspartic acid.

The compounds of this invention can be prepared (Review: A. Sausis, G. Duburs; *Heterocycles*, 27, 269 (1988)), for example, by reaction of a compound of the formula (III) and methyl acetoacetate (IV) by heating (under reflux) in the presence or absence of an organic solvent (e.g., methanol, ethanol, propanol, isopropanol, benzene, toluene, dioxane, tetrahydrofuran, dimethyl sulfoxide and dimethylformamide), to produce a compound of the formula (V) followed by reaction of a compound of formula (V) and 3-aminocrotonic acid methyl ester (VI) under the same conditions as above, to obtain a 1,4-dihydropyridine derivative (VII). A compound of the formula (VII) and a compound of formula $R^6$-X (VIII) are then reacted in an inert organic solvent (e.g., dioxane, tetrahydrofuran, dimethyl sulfoxide and dimethylformamide) in the presence of sodium hydride. This reaction procedure is summarized in the following schematic:

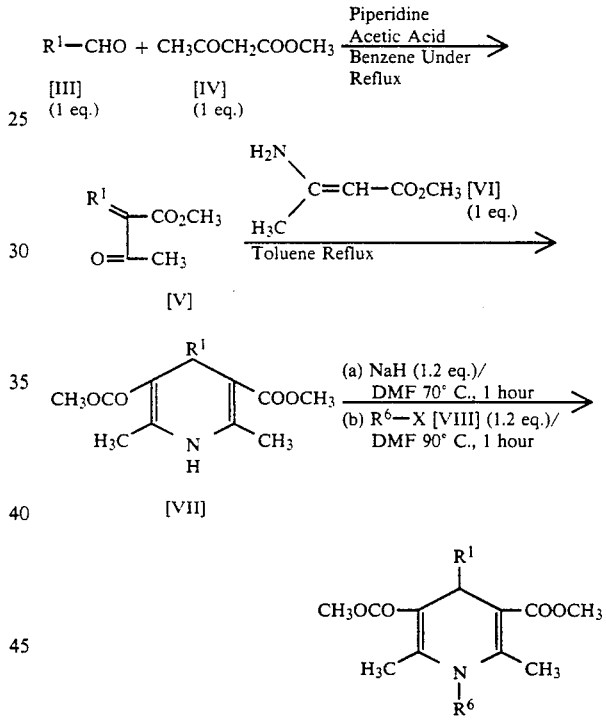

wherein $R^1$ and $R^6$ are as defined above, and X is a replaceable group commonly employed in organic synthesis (e.g., halogen or p-toluenesulfonyloxy).

The reaction product thus formed (a compound of formula (I)) can be easily isolated from the reaction mixture and purified by using commonly used techniques, such as solvent extraction, chromatography and crystallization, e.g., as described in L. F. Fieser, *Experiments in Organic Chemistry*.

As described herein, the compounds of the formula (I) and/or (II) are effective when used in combination with anti-cancer agents to enhance the effectiveness thereof against tumor cells with acquired multi-drug resistance. Specific examples of anti-cancer agents, with which the compounds of the present invention can be used include vinca alkaloid agents such as vincristine and vinblastin, antibiotics, for example, anthracyclin (e.g. adriamycin) and bleomycin, nucleic acids such as 5-fluoro urasil, cisplatin, and etoposide. These agents can be used at the same doses as those employed in conventional chemotherapy.

The 1,4-dihydropyridine derivatives used in the present invention are useful as agents against drug resistant tumors in mammals including humans. The derivatives in combination with anti-cancer agents, e.g., as described above, can be used for cancer therapy by formulating them into a preparation such as tablets, capsules, and elixirs for oral administration and into an aseptic liquid preparation or an aseptic suspension preparation for parenteral administration such as subcutaneous, intramuscular, intravenous injection, and suppositories. The 1,4-dihydropyridine derivatives of the present invention can be administered to a subject necessitating such treatment (animals and humans) in a dosage range of 1 to 1,000 mg per subject generally several times a day, that is, at a total daily dosage of 1 to 3,000 mg. The dosage varies according to the seriousness of the disease, the body weight of the subjects, and other factors recognized by those skilled in the art.

To produce the preparations using the 1,4-dihydropyridine derivatives as described above of the present invention, they may be converted into dosage forms such as tablets, granules, powders, capsules, injections and suppositories by conventional methods.

For the production of oral preparations, the 1,4-dihydropyridine derivative or a mixture of the 1,4-dihydropyridine derivative and an anti-cancer agent is used as the principal agent and adjuvants such as fillers, binders, disintegrators, lubricants, colorants, and correctives, as necessary, are added thereto and then such is formed by conventional methods into tablets, coated tablets, granules, powders, capsules and the like.

Examples of specific materials which can be incorporated into tablets, capsules, and so forth are as follows: fillers such as cornstarch, lactose, white sugar, glucose, sorbitol, and crystalline cellulose; binders such as polyvinyl alcohol, polyvinyl ether, ethyl cellulose, methyl cellulose, gum arabic, tragacanth gelatin, shellac, hydroxypropyl cellulose, hydropropyl starch, polyvinyl pyrrolidone, disintegrators such as starch, agar, gelatin powder, crystalline cellulose, calcium carbonate, sodium bicarbonate, calcium citrate, dextrin and pectin, lubricants such as magnesium stearate, talc, polethylene glycol, silica, hardened plant oil; colorants such as those which are allowed as an additive for medicines; correctives such as cocoa powder, mentha herb, aromatic acids, mentha oil, borneol and cinnamon bark powder. These tablets and granules may be coated with sugar, gelatin, or the like, as desired.

For the production of the injectable formulations, there may be added to the derivative or a mixture of 1,4-dihydropyridine and anti-cancer agent as the principal agent, a pH adjusting agent, a buffer agent, a stabilizing agent, preservatives or the like, as necessary, to produce a material for subcutaneous, intramuscular or intravenous injection by conventional methods.

This invention is further illustrated by the following examples which are not to be construed as limiting the scope of the present invention. Unless otherwise indicated herein, all parts, percents, ratios and the like are by weight.

EXAMPLE 1

Synthesis of Dimethyl 1,4-Dihydro-4-(3,4-dimethoxyphenyl)-2,6-dimethyl-1-(3-phenylpropyl)3,5-pyridinedicarboxylate a. Synthesis of Methyl 2-(3,4-Dimethoxybenzylidene)-acetoacetate)

To a solution of 54.8 g (0.33 mol) 3,4-dimethoxybenzaldehyde and 34.8 mg (0.3 mol) methyl acetoacetate in 20 ml benzene, were added dropwise 1.02 g (12 mmol) piperidine and 3.66 g (61 mmol) acetic acid in that order, and water was removed from the mixture by heating in a Dean-Stark apparatus until water was no longer distilled off. The solvents were distilled off from the reaction mixture, and the oil thus left was allowed to stand for five days. The crystals which separated out were collected by filtration, giving 41.1 g (52%) of methyl 2-(3,4-dimethoxy-benzylidene)acetoacetate as yellow crystals. M.P.: 93°–95° C.

b. Synthesis of Dimethyl 1,4-Dihydro-4-(3,4-dimethoxyphenyl)-2,6-dimethyl-3,5-pyridinedicarboxylate A solution of 5.0 g (18.9 mmol) 2-(3,4-dimethoxybenzylidene)acetoacetate and 2.18 g (18.9 mmol) 3-aminocrotonic acid methyl ester in 100 ml toluene was heated in a Dean-Stark apparatus for water removal, the solvent was distilled off from the reaction mixture, and the residue was purified by column chromatography (SiO$_2$/CHCl$_3$), giving 4.30 g (63%) of dimethyl 1,4-dihydro-4-(3,4-dimethoxyphenyl)-2,6-dimethyl-3,5-pyridinedicarboxylate as whitish yellow crystals. M.P.: 153.5°–155° C.

c. Synthesis of Dimethyl 1,4-Dihydro-4-(3,4-dimethoxyphenyl)-2,6-dimethyl-1-(3-phenylpropyl) -3,5-pyridinedicarboxylate 60% Sodium hydride (0.26 g) was washed with several milliliters of anhydrous n-hexane in an argon gas atmosphere, and 10 ml dimethylformamide was added. To the resulting mixture, was added dropwise 20 ml of a dimethylformamide solution containing 2 g (5.5 mmol) dimethyl 1,4-dihydro-4-(3,4-dimethoxyphenyl)-2,6-dimethyl-3,5-pyridinedicarboxylate with stirring. The mixture was heated at 90° C. for one hour, 20 ml of a dimethylformamide solution of 3-phenylpropyl bromide was then added, and heating at 90° C. was continued for one hour. After cooling the mixture to room temperature, 20 ml diethyl ether was added, the resulting mixture was washed with water, and the solvent was distilled off under reduced pressure. The crude product thus obtained was purified by column chromatography (SiO$_2$/n-hexane-ethyl acetate 2:1), affording 0.8 g (30%) of the pure product. M.P.: 97°–98° C.

EXAMPLES 2 THROUGH 46

The compounds listed in Table 1 below were prepared in the same manner as in Example 1:

| Example No. | Starting Material, $R^6$-X | Product | Yield (%) | M.p. (°C.) |
| --- | --- | --- | --- | --- |
| 2 | Methyl iodide | Dimethyl 1,4-dihydro-4-(3,4-dimethoxyphenyl)-2,6-dimethyl-1-methyl-3,5-pyridinedicarboxyl- | 48 | 155.5–157.5 |

-continued

| Example No. | Starting Material, $R^6$-X | Product | Yield (%) | M.p. (°C.) |
|---|---|---|---|---|
| 3 | Ethyl chloroformate | Dimethyl 1,4-dihydro-4-(3,4-dimethoxyphenyl)-2,6-dimethyl-1-ethoxycarbonyl-3,5-pyridinedicarboxylate | 67 | 58–60 |
| 4 | 3-Phenoxypropyl bromide | Dimethyl 1,4-dihydro-4-(3,4-dimethoxyphenyl)-2,6-dimethyl-1-(3-phenoxypropyl)-3,5-pyridinedicarboxylate | 17 | 107–108.5 |
| 5 | 4-Phenylbutyl bromide | Dimethyl 1,4-dihydro-4-(3,4-dimethoxyphenyl)-2,6-dimethyl-1-(4-phenylbutyl)-3,5-pyridinedicarboxylate | 40 | 108–109 |
| 6 | 5-Phenylpentyl bromide | Dimethyl 1,4-dihydro-4-(3,4-dimethoxyphenyl)-2,6-dimethyl-1-(5-phenylpentyl)-3,5-pyridinedicarboxylate | 32 | 84–84.5 |
| 7 | 4-Phenoxybutyl bromide | Dimethyl 1,4-dihydro-4-(3,4-dimethoxyphenyl)-2,6-dimethyl-1-(4-phenoxybutyl)-3,5-pyridinedicarboxylate | 20 | Oil |
| 8 | 4-(4-Methoxyphenyl)butyl bromide | Dimethyl 1,4-dihydro-4-(3,4-dimethoxyphenyl)-2,6-dimethyl-[4-(4-methoxyphenyl)butyl]-3,5-pyridinedicarboxylate | 47 | Oil |
| 9 | 3-Phenylpropyl bromide | Dimethyl 1,4-dihydro-4-(3,4-dichlorophenyl)-2,6-dimethyl-1-(3-phenylpropyl)-3,5-pyridinedicarboxylate | 52 | 98–99 |
| 10 | Benxyl bromide | Dimethyl 1,4-dihydro-4-(3,4-dimethoxyphenyl)-1-benzyl-3,5-pyridinedicarboxylate | 65 | 131–132 |
| 11 | 3-Phenylpropyl bromide | Dimethyl 1,4-dihydro-4-chlorophenyl)-2,6-dimethyl-1-(3-phenylpropyl)-3,5-pyridinedicarboxylate | 55 | 126–128 |
| 12 | 3-Phenylpropyl bromide | Dimethyl 1,4-dihydro-4-(3,4,5-trimethoxyphenyl)-2,6-dimethyl-1-(3-phenylpropyl)-3,5-pyridinedicarboxylate | 45 | 130–131 |
| 13 | 3-Phenylpropyl bromide | Dimethyl 1,4-dihydro-4-(3,chlorophenyl)-2,6-dimethyl-1-(3-phenylpropyl)-3,5-pyridinedicarboxylate | 52 | 79–80 |
| 14 | | (CANCELED) | | |
| 15 | 3-Phenylpropyl bromide | Dimethyl 1,4-dihydro-4-phenyl-2,6-dimethyl-1-(3-phenylpropyl)-3,5-pyridinedicarboxylate | 58 | 112–113 |
| 16 | 3-Phenylpropyl bromide | Dimethyl 1,4-dihydro-4-(4-fluorophenyl)-2,6-dimethyl-1-(3-phenylpropyl)-3,5-pyridinedicarboxylate | 55 | 89–90 |
| 17 | 3-Phenylpropyl bromide | Dimethyl 1,4-dihydro-4-(4-methoxyphenyl)-2,6-dimethyl-1-(3-phenylpropyl)-3,5-pyridinedicarboxylate | 56 | 116–117 |
| 18 | 3-Phenylpropyl bromide | Dimethyl 1,4-dihydro-4-3-(methoxyphenyl)-2,6-dimethyl-1-(3-phenylpropyl)-3,5-pyridinedicarboxylate | 56 | 104–105 |
| 19 | 3-Phenylpropyl bromide | Dimethyl 1,4-dihydro-4-(nitrophenyl)-2,6-dimethyl-1-(3-phenylpropyl)-3,5-pyridinedicarboxylate | 59 | 146–147 |
| 20 | 3-Phenylpropyl bromide | Dimethyl 1,4-dihydro-4-(3-nitrophenyl)-2,6-dimethyl-1-(3-phenylpropyl)-3,5-pyridinedicarboxylate | 54 | 123–124 |

-continued

| Example No. | Starting Material. $R^6$-X | Product | Yield (%) | M.p. (°C.) |
|---|---|---|---|---|
| 21 | 3-Phenylpropyl bromide | Dimethyl 1,4-dihydro-4-(4-methylphenyl)-2,6-dimethyl-1-(3-phenylpropyl)-3,5-pyridinedicarboxylate | 59 | 117–118 |
| 22 | 3-Phenylpropyl bromide | Dimethyl 1,4-dihydro-4-(3-methylphenyl)-2,6-dimethyl-1-(3-phenylpropyl)-3,5-pyridinedicarboxylate | 57 | 93–94 |
| 23 | | (CANCELED) | | |
| 24 | 3-Phenylpropyl bromide | Diethyl 1,4-dihydro-4-(3,4-dimethoxyphenyl)-2,6-dimethyl-1-(3-phenylpropyl)-3,5-pyridinedicarboxylate | 42 | oil |
| 25 | 3-Phenylpropyl bromide | Dibenzyl 1,4-dihydro-4-(3,4-dimemethoxyphenyl)-2,6-dimethyl-1-(3-phenylproyl)-3,5-pyridinedicarboxylate | 58 | oil |
| 26 | 3-Phenylpropyl bromide | Ethyl 1,4-dihydro-4-(3,4-dimethoxyphenyl)-1-(3-phenylpropyl)-3-cyano-5-pyridinedicarboxylate | 79 | oil |
| 27 | | (CANCELED) | | |
| 28 | | (CANCELED) | | |
| 29 | 4-Cyclohexyl pyl bromide | Dimethyl 1,4-dihydro-4-(3,4-dimethoxyphenyl)-2,6-dimethyl-1-(4-cyclohexylbuhyl)-3,5-pyridinedicarboxylate | 55 | oil |
| 30 | 3-Phenylpropyl bromide | Methyl 1,4-dihydro-4-(3,4-dimethoxyphenyl)-2,6-dimethyl-1-(3-phenylpropyl)-3-cyano-5-pyridinedicarboxylate | 68 | oil |
| 31 | 3-Phenylpropyl bromide | Dimethyl 1,4-dihydro-4-(3,4-dimethoxyphenyl)-2,6-diethyl-1-(3-phenylpropyl)-3,5-pyridinedicarboxylate | 35 | oil |
| 32 | 3-Phenylpropyl bromide | 1,4-Dihydro-4-(3,4-dimethoxyphenyl)-2,6-dimethyl-1-(3-phenylpropyl)-3,5-dicyanopyridine | 49 | oil |
| 33 | 3-Phenylpropyl bromide | Dimethyl 1,4-dihydro-4-(2-naphthyl)-2,6-dimethyl-1-(3-phenylpropyl)-3,5-pyridinedicarboxylate | 28 | oil |
| 34 | 3-Phenylpropyl bromide | Dimethyl 1,4-dihydro-4-(1-naphthyl)-2,6-dimethyl-1-(3-phenylpropyl)-3,5-pyridinedicarboxylate | 42 | oil |
| 35 | 3-Phenylpropyl bromide | Dimethyl 1,4-dihydro-4-(3-methoxy,4-benzyloxyphenyl)-2,6-dimethyl-1-(3-phenylpropyl)-3,5-pyridinedicarboxylate | 47 | oil |
| 36 | 3-Phenylpropyl bromide | Dimethyl 1,4-dihydro-4-(3,4-diethoxy)-2,6-dimethyl-1-(3-phenylpropyl)-3,5-pyridinedicarboxylate | 53 | oil |
| 37 | 3-Phenylpropyl bromide | Ethyl 1,4-dihydro-4-(2-bromo, 4,5-dimethoxyphenyl)-nyl)-2,6-dimethyl-1-(3-phenylpropyl)-3,5-pyridinedicarboxylate | 72 | oil |
| 38 | 3-Phenylpropyl bromide | tert-Butyl-1-4,dihydro-4-(3,4-dimethoxyphenyl)-2,6-dimethyl-1-(3-phenylpropyl)-3,5-pyridinedicarboxylate | 54 | oil |
| 39 | 3-Phenylpropyl bromide | Dimethyl 1,4-dihydro-4-(3,4-methylenedioxyphenyl)-2,6-dimethyl-1-(3-phenylpropyl)-3,5-pyridinedicarboxylate | 52 | 95–96 |
| 40 | 3-Phenylpropyl bromide | Dimethyl 1,4-dihydro-4-(2,3,4-trimethoxyphenyl)-2,6-dimethyl-1-(3-phenylpropyl)-3,5-pyridinedicar- | 33 | oil |

-continued

| Example No. | Starting Material. R⁶-X | Product | Yield (%) | M.p. (°C.) |
|---|---|---|---|---|
| 41 | 3-Phenylpropyl bromide | Dimethyl 1,4-dihydro-4-2,4,5-trimethoxyphenyl)-2,6-dimethyl-1-(3-phenylpropyl)-3,5-pyridinedicarboxylate | 60 | 157-158 |
| 42 | 3-Phenylpropyl bromide | Dimethyl 1,4-dihydro-4-(3,4-di-methoxyphenyl)-2,6-dimethyl-1-(3-phenylproionyl)-3,5-pyridinedicarboxylate | 59 | oil |
| 43 | 3,3-Diphenylpropyl bromide | Dimethyl 1,4-dihydro-4-(3,4-dimethoxyphenyl)-2,6-dimethyl-1-(3-diphenylpropyl)-3,5-pyridinedicarboxylate | 67 | oil |
| 44 | Gernayl bromide | Dimethyl 1,4-dihydro-4-(3,4-dimethoxyphenyl)--2,6-dimethyl-1-gernayl-3,5-pyridinedicarboxylate | 25 | oil |
| 45 | 3-Phenylpropyl bromide | Dimethyl 1,4-dihydro-4-(2,4-dimethoxyphenyl)-2,6-dimethyl-1-(3-phenylpropyl)-3,5-pyridinedicarboxylate | 53 | 120-121 |
| 46 | 4-(3,4-Dimethoxyphenyl)-4-cyano-4-isopropylbutyl bromide | Dimethyl 1,4-dihydro-4-(2,4-dimethoxyphenyl)-2,6-dimethyl-1-[4-(3,4-dimethoxypropyl)-4-cyano-4-isopropylbutyl]-3,5-pyridinedicarboxylate | 35 | oil |

EXAMPLE 47

Synthesis of 1,4-Dihydro-4-(3,4-dimethoxyphenyl)-2,6-dimethyl-1-(3-phenylpropyl) -3,5-pyridinedicarboxylic Acid 3-Methyl Ester

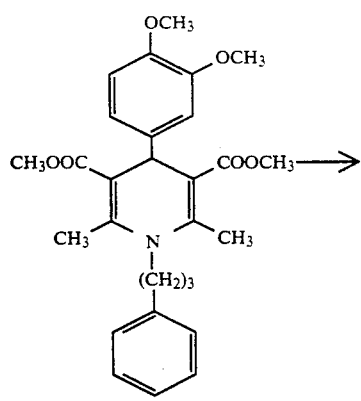

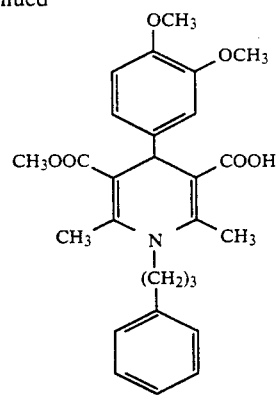

To a solution of 3.31 g (6.9 mmol) of 1,4-dihydro-4-(3,4-dimethoxyphenyl) -2,6-dimethyl-1-(3-phenylpropyl)-3,5-pyridinecarboxylic acid-3, 5-dimethyl ester in 15 ml of methanol was added 10 ml of 1N NaOH/water and the mixture was cooled and extracted with $CH_2Cl_2$. The extract was dried and concentrated. The resulting residue was purified by column chromatography ($SiO_2$/AcOEt:Hexane 1:1) to give 0.7 5g (2.1 mmol) of 1,4-dihydro-4-(3,4-dimethoxyphenyl)-2,6-dimethyl-1-(3-phenylpropyl) -3,5-pyridinedicarboxylic acid-3-methyl ester.

EXAMPLE 48

Synthesis of
1,4-Dihydro-4-(3,4-dimethoxyphenyl)-2,-6-dimethyl-1-(3-phenylpropyl) -3,5-pyridinedicarboxylic acid 3-Ethylether Ester

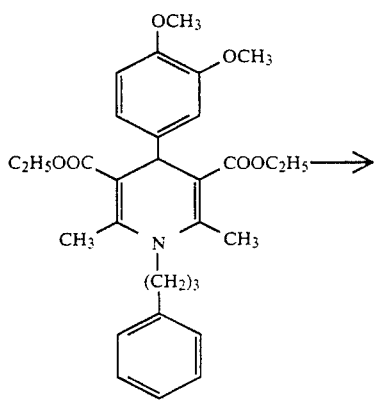

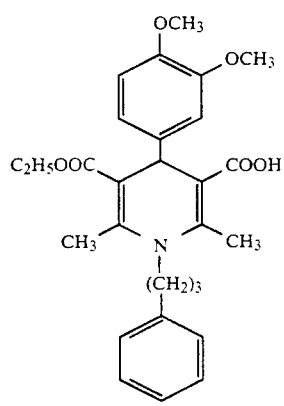

The procedures of Example 47 were used and the product purified by column chromatography (5% MeOH/CH₂Cl₂).

EXAMPLE 49

Synthesis of
1,4-Dihydro-4-(3,4-dimethoxyphenyl)-2,6-dimethyl-1-(3-phenylpropyl) -3-cyano-5-hydroxymethylpyridine

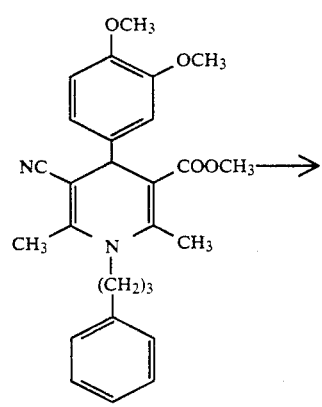

-continued

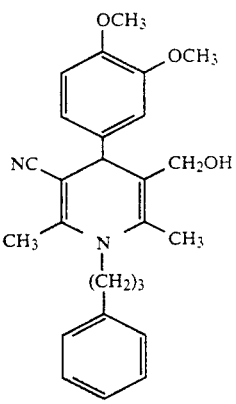

To a solution of 1.48 g (3.32 mmol) of 1.4-dihydro-4-(3,4-dimethoxyphenyl)-2,6-dimethyl -1-(3-phenylpropyl)-3-cyano-5-pyridine carboxylic acid-5-methylester in 42 ml of dry tetrahydrofuran (THF) was added with stirring 1.8 ml of 1N LiAlH₄/diethyl ether solution at room temperature (about 20°-30° C.). The mixture was stirred for 20 min. and was poured into ice-water. The mixture was filtered and extracted with CH₂Cl₂. This oil was purified by column chromatography (AcO-Et:Hexane 1:1) to give 1.08 g (2.58 mmol) of 1,4-dihydro-4-(3,4-dimethoxyphenyl-2,6-dimethyl -1-(3-phenylpropyl)-3-cyano-5-hydroxymethylpyridine (78% yield: oil).

EXAMPLE 50

Synthesis of
1,4-Dihydro-4-(3,4-dimethylphenyl)-2,6-dimethyl-1-(3-phenylpropyl) -3-cyano-5-formylpyridine

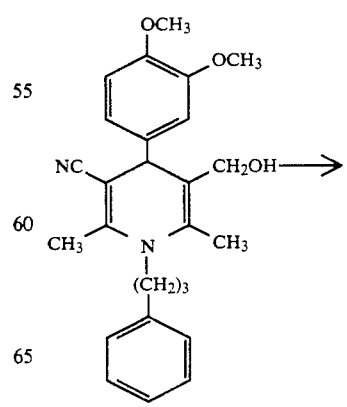

-continued

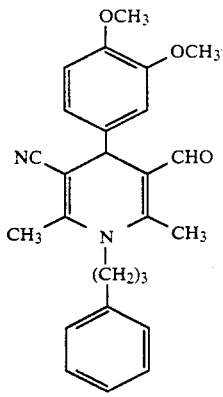

To a solution of 13 mg (0.026 mmol) of 1,4-dihydro-4-(3,4-dimethoxyphenyl)-2,6-dimethyl-1-(3-phenylpropyl) -3-cyano-5-hydroxymethylpyridine in 0.45 ml of dichloroethane was added 5 mg of activated manganese dioxide. The mixture was heated at 80° C. for one hour. Then the mixture was filtered and concentrated. The resulting residue was purified by thin layer chromatography (AcOEt:Hexane 1:1) to give 7.4 mg (0.015 mmol) of 1,4-dihydro-4-(3,4-dimethoxyphenyl)-2,6-dimethyl -1-(3-phenylpropyl)-3-cyano-5-formylpyridine (yield: 58%).

EXAMPLE 51

Synthesis of 1,4-Dihydro-4-(3,4-dimethoxyphenyl)-3,5-pyridinedicarboxylic acid 3,5-Dimethyl Ester A mixture of 4.3 g (51 mmol) methyl propiolate, 4.2 g (6 mmol) of veratraldehyde, 4.5 g (58 mmol) of ammonium acetate and 4.5 ml of acetic acid were heated at 60° C. for 20 min. The solution was poured into ice-water and the aqueous phase was extracted with $CH_2Cl_2$. The extract was dried and concentrated to give a yellow oil. This oil was crystallized from methanol to give 2.8 g (8.4 mmol) of 1,4-dihydro-4-(3,4-dimethoxyphenyl)-3,5-pyridinedicarboxylic acid-3,5-dimethyl ester. (yield: 32%)

This product was alkylated using phenylpropyl bromide as described in Example 1 to give 2.5 g (5.5 mmol) of 1,4-dihydro-4-(3,4-dimethoxyphenyl)-1-(3-phenylpropyl) -3,5-pyridinedicarboxylic acid-3,5-dimethyl ester (yield: 67%, M.P. 107°-113° C.)

EXAMPLES 52 THROUGH 79

The compounds listed in Table 2 below were prepared in the same manner as described in Example 1.

TABLE 2

| Example No. | Product |
|---|---|
| 52 | R = (CH₂CH₂-CH=CH-phenyl, trans) |
| 53 | R = (CH₂CH₂-CH=CH-phenyl, cis) |
| 54 | R = (CH₂-cyclopropyl-phenyl) |
| 55 | R = (CH₂-cyclopropyl-phenyl) |
| 56 | R = (CH₂CH₂-CH(O)-CH₂-phenyl, epoxide) |
| 57 | R = $-(CH_2)_5-CH_3$ |
| 58 | R = $-CH_2CH_2CH_2CH_2CH=CH_2$ |
| 59 | R = $-CH_2CH_2CH_2CH=CH_2$ |
| 60 | R = (CH₂CH₂CH₂-naphthyl) |

TABLE 2-continued
| Example No. | Product |
|---|---|
| 61 | R = 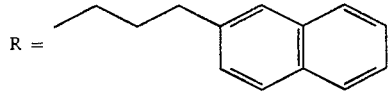 |
| 62 | R = 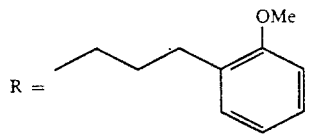 |
| 63 | R = 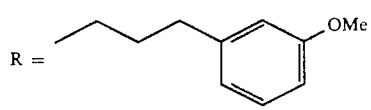 |
| 64 | R = 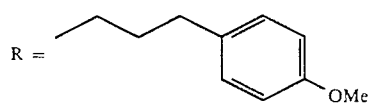 |
| 65 | R = 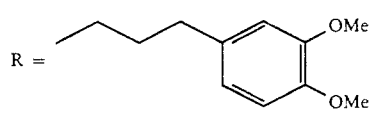 |
| 66 | R = 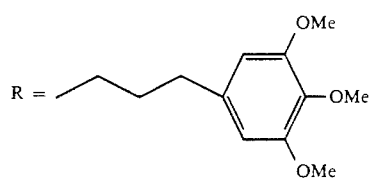 |
| 67 | 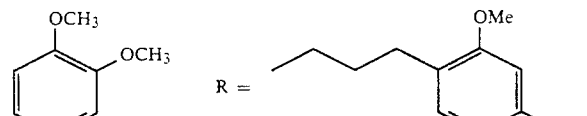 R = 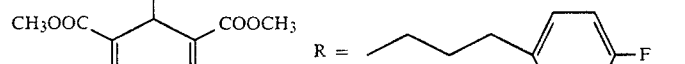 |
| 68 | R = 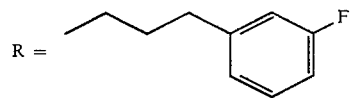 |
| 69 | R = 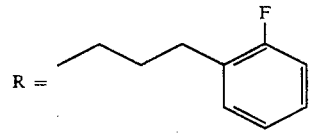 |
| 70 | R = 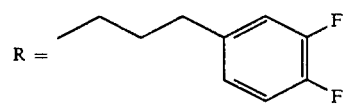 |
| 71 | R = 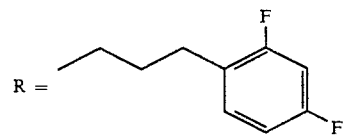 |
| 72 | R = |

TABLE 2-continued

| Example No. | Product |
|---|---|
| 73 | 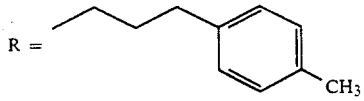 R = (butyl)-C6H4-4-CH3 |
| 74 | 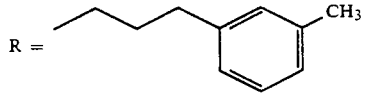 R = (butyl)-C6H4-3-CH3 |
| 75 | 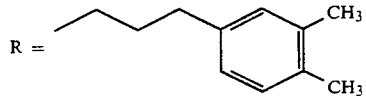 R = (butyl)-C6H3-3,4-(CH3)2 |
| 76 | 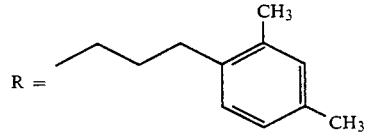 R = (butyl)-C6H3-2,4-(CH3)2 |

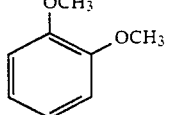

| Ex. | $R^2$ | $R^3$ | $R^4$ | $R^5$ |
|---|---|---|---|---|
| 77 | —CHO | —CHO | H | H |
| 78 | —CN | —CO$_2$CH$_3$ | —CH$_3$ | —CH$_3$ (R-isomer) |
| 79 | —CN | —CO$_2$CH$_3$ | —CH$_3$ | —CH$_3$ (S-isomer) |

EXAMPLE 80

Evaluation of Effect Against Drug-Resistant Tumor Cells

Tumor cells resistant to adriamycin (AD), AD$_{10}$, were dispensed at a concentration of 100×10$^4$ cell/ml/well and incubated for one day. The medium was replaced with 0.5 ml of RPMI 1640-5%FBS-KM-10 mM Hepes B, and 5 μl of each test drug solution (prepared by dissolving the drug in dimethyl sulfoxide (DMSO), followed by dilution with PBS) was added to final concentrations of 0.1 μg/ml and 1 μg/ml. After incubation in an CO$_2$-incubator for two hours, the cells were washed five times with 5 ml of ice-cooled PBS containing vincristine (VCR), 0.5 ml of 0.2N-NaOH solution was added, and the mixture was transferred to vials, which were heated at 56° C. for 30 to 60 minutes to lyse the cells. Acid-Aquasal (24 ml) was added, the amount of ($^3$H)VCR taken inside the cells was measured using a liquid scintiallation counter, and the effect against drug-resistant tumor cells was evaluated by the percentage of take-in ($^3$H)VCR amount based on the value for the control (the take-in amount when no drug was used). The results obtained are shown in Table 3 below.

TABLE 3

| | Effect Against Drug-Resistant Tumor Cells (% to control) | |
|---|---|---|
| Example No. | Drug Concn. (1.0 μg/ml) | Drug Concn. (10 μg/ml) |
| 1 | 767 | 2058 |
| 2 | 122 | 157 |
| 3 | 144 | 458 |
| 4 | 461 | 1675 |
| 5 | 538 | 1769 |
| 6 | 386 | 1835 |
| 7 | 287 | 1573 |
| 8 | 268 | 1717 |
| 10 | 168 | 1462 |
| 12 | 356 | 1809 |
| 15 | 140 | 1075 |
| 16 | 151 | 1206 |
| 17 | 204 | 1284 |
| 18 | 160 | 943 |
| 23 | 225 | 1298 |
| 26 | 278 | 1324 |
| 27 | 225 | 1298 |
| 29 | 198 | 1114 |
| 30 | 356 | 2110 |
| 31 | 220 | 1048 |
| 32 | 348 | 1861 |
| 36 | 253 | 1625 |
| 49 | 223 | 1297 |
| 51 | 281 | 1835 |

EXAMPLE 81

Evaluation of Side-Effects (hypotensive effect)

In this example, six, well acclimated, male SHR (spontaneous hypertensive rats; weighing 400 to 440 grams) were used as test animals.

One milliliter of physiological saline containing a test sample (10 mg/Kg), nicor (2.5% of the test sample) and ethanol (2.5% of the test sample) was injected intravenously once into each rat, and the blood pressure was measured by the plethysmographic tail method. The results obtained are shown in Table 4 below.

TABLE 4

| Example No. | Time After Administration (hr) | Maximum Decrease In Blood Pressure (mmHg) |
| --- | --- | --- |
| 2 | 0.5 | 0 |
| 3 | 0.5 | 0 |
| 4 | 0.5 | 0 |

As is apparent from the foregoing, the 1,4-dihydropyridine derivatives of this invention exhibit high effects against drug-resistant tumor cells and show low hypotensive effect. The compounds of this invention are therefore of great value in the pharmaceutical industry.

While the invention has been described in detail and with reference to specific embodiments thereof, it will be apparent to one skilled in the art that various changes and modifications can be made therein without departing from the spirit and scope thereof.

What is claimed is:

1. A 1,4-Dihydropyridine derivative which is dimethyl 1,4-dihydro-4-(3,4-dimethoxyphenyl)-2,6-dimethyl-1-(3-phenoxypropyl)-3,5-pyridinedicarboxylate represented by the following formula (III):

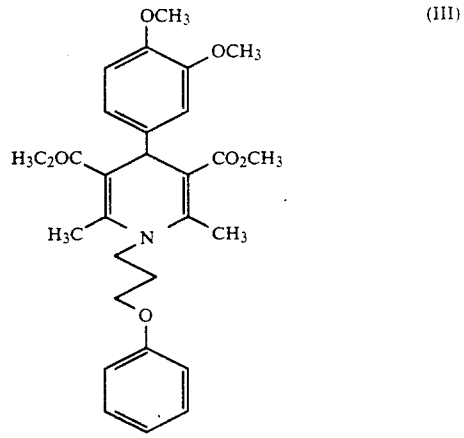

2. A 1,4-Dihydropyridine derivative which is 1,4-dihydro-4-(3,4-dimethoxyphenyl)-2,6-dimethyl-1-(3-benzyloxypropyl)-3,5-pyridinedicarboxylic acid 3,5-dimethyl ester.

3. A 1,4-Dihydropyridine derivative which is 1,4-dihydro-4-(3,4-dimethoxyphenyl)-2,6-dimethyl-1-[3-(4-benzoylphenoxy)propyl]-3,5-pyridinedicarboxylic acid 3,5-dimethyl ester.

* * * * *